(12) United States Patent
Lai et al.

(10) Patent No.: US 8,038,777 B2
(45) Date of Patent: Oct. 18, 2011

(54) AIR STERILIZATION DEVICE WITH LOW AEROSOL BOUNCE

(75) Inventors: Chane-Yu Lai, Shetou Township, Changhua County (TW); Po-Chen Hung, Taipei (TW); Sheng-Hsiu Huang, Jhongli (TW); Yu-Fang Ho, Taipei (TW); Cheng-Ping Chang, Taipei (TW); Tung-Sheng Shih, Taipei (TW); Tai-Shan Yu, Taipei (TW); Chi-yu Chuang, Sijhih (TW)

(73) Assignee: Institute of Occupational Safety and Health, Council of Labor Affairs, Executive Yuan, Taipei County (TW)

( * ) Notice: Subject to any disclaimer, the term of this patent is extended or adjusted under 35 U.S.C. 154(b) by 434 days.

(21) Appl. No.: 12/292,222

(22) Filed: Nov. 14, 2008

(65) Prior Publication Data

US 2009/0162251 A1 Jun. 25, 2009

(30) Foreign Application Priority Data

Dec. 25, 2007 (TW) .............................. 96149853 A

(51) Int. Cl.
*B01D 50/00* (2006.01)
(52) U.S. Cl. ......... 96/224; 55/524; 55/DIG. 24; 95/285; 422/4; 422/24; 422/121; 422/186.3

(58) Field of Classification Search ................. 55/385.1; 95/28, 159, 273; 96/223, 224, 226; 422/54, 422/186.01, 186.07, 186.3; 361/230, 231, 361/233

See application file for complete search history.

(56) References Cited

U.S. PATENT DOCUMENTS

| 5,891,221 | A | * | 4/1999 | Rohrbach et al. | 95/159 |
| 7,326,387 | B2 | * | 2/2008 | Arts et al. | 422/186.3 |
| 7,824,469 | B2 | * | 11/2010 | Chan et al. | 95/28 |
| 2002/0144601 | A1 | * | 10/2002 | Palestro et al. | 95/273 |
| 2004/0250683 | A1 | * | 12/2004 | Soane et al. | 96/226 |
| 2009/0133582 | A1 | * | 5/2009 | Snowball | 96/224 |

* cited by examiner

*Primary Examiner* — Duane Smith
*Assistant Examiner* — Minh-Chau Pham
(74) *Attorney, Agent, or Firm* — Rosenberg, Klein & Lee

(57) ABSTRACT

An air sterilization device with low aerosol bounce includes an air conditioning pipe, a porous filter media, and a UV light generator. This porous filter media, it is secured on the fixing portion. This porous filter media has many irregularly distributed channels. The channel is coated with a coating layer having a thickness between 10 μm to 1000 μm sticking aerosols for avoiding bounce effect. The UV light generator can emit UV light to kill biological aerosols. It is suitable for long-term usage. So, the bounce effect of aerosols can be significantly reduced. The maintenance cost is low. The sterilization effect is excellent. Plus, the flow rate of the air conditioning system remains high.

6 Claims, 8 Drawing Sheets

AIR STERILIZATION DEVICE WITH LOW AEROSOL BOUNCE

BACKGROUND OF THE INVENTION

1. Field of the Invention

The present invention relates to an air sterilization device with low aerosol bounce. Particularly, it relates to an air sterilization device that contains a porous filtration media with a coating layer and a UV (ultraviolet) light generator. So, the bounce effect of aerosols can be significantly reduced. The maintenance cost is low. The germicidal effective rate is excellent. Plus, the flow rate of the air conditioning system remains high.

2. Description of the Prior Art

The conventional air sterilization methods at least include: using a filter to capture the solid aerosols in the air, utilizing UV light to emit on bacteria in the air directly; coating with a photocatalysis layer to cooperate with a UV light source to activate the photo-catalytic reaction in order to kill the bacteria, etc.

The first conventional method is to use a filter to capture the solid aerosols in the air. Referring to FIGS. 1 and 2, the conventional air conditioning system has a pipeline 90 (or ventilation duct). A general filter 80 is installed in a proper position (such as near the fresh air entrance or near exit) of this pipeline 90. This general filter 80 has a thickness X. The general filter 80 consists of many filtration fibers 81. There are many small openings 82 among the filtration fibers 81 for allowing air to flow through. The porosity of a general filter 80 is large; therefore the flow resistance (or called pressure drop) is small. The flow resistance and price of the filtration fibers 81 are significantly lower than the ones of foam or the ones of a high efficiency particulate air filter (or briefly referred as HEPA filter). As shown in FIG. 3, the eighteenth curve L18 represents a general filter 80. The nineteenth curve L19 represents foam. The twentieth curve L20 represents the HEPA filter. Theoretically, dusts or particles in the airstream can be captured by the filter fibers 81 based on the single fiber theory. The single fiber theory includes gravitational settling, inertial impaction, interception, diffusion, and electrostatic attraction. Because the porosity of the general filter is too large and the packing density of the filter is too small, the filtration efficiency cannot be increased. As a result, the collecting efficiency of the general filter is low. It is also lower than the one of the foam or the HEPA. Referring to FIG. 4, concerning the penetration rate of aerosols, the eighteenth curve L18 represents a general filter 80. The nineteenth curve L19 represents foam. The twentieth curve L20 represents the HEPA filter. Therefore, in order to achieve the high filtration efficiency, low flow resistance is required, because the flow resistance will significantly influence the energy consumption. Moreover, a good filter must have an excellent collecting efficiency and low flow resistance. That is, it must have a satisfactory filter quality (briefly referred as $q_F$). The filter quality can be defined by the following equations (1) and (2).

$$q_F = \frac{-\ln P}{\Delta p} \tag{1}$$

$$P = 1 - E_{ff} \tag{2}$$

where
P: aerosol penetration;
Δp: flow resistance (or pressure drop);
$E_{ff}$: collection efficiency.

The flow resistance is the overall loss for the air flow through this filter, and is proportional to the filter thickness, packing density, flow velocity and the total surface area of the filter fibers. Hence, if the collection efficiency increases, the flow resistance also increases. By reducing filter flow velocity and adding more filter material in the same filter volume, the filter collection efficiency will improve. However, it increases the total cost for filter material. It is possible to happen that some of the solid aerosols 83 (or particles) with greater inertial force impact on the filter fibers 81 and then bounce off, as illustrated in FIG. 5 (the effect of bounce off). It will make some aerosols 83 to occur the re-entrainment phenomenon. Therefore, many aerosols 83 continue to penetrate through the filter material. It significantly reduces the collecting efficiency of the filter. For most air condition system (including heating, ventilating and air conditioning, briefly called HVAC), the flow velocity in the pipeline is high as in the range of 50~300 cm/s (or even higher) depending on the capacity and application scope of the air conditioning system. Thus, once the flow velocity increases, the flow resistance increases, too.

The second conventional method is to utilize UV light to emit on bacteria in the air directly. The best wavelength of UV light is 253.7 nm (in the range of Ultraviolet C, short wave; briefly called UV-C; 280 nm-100 nm). However, the flow velocity in the pipeline is roughly 50~300 cm/s. The aerosols carried by the airstream are also moving at that velocity. Under such high flow velocity, the time of UV light exposure is too short to kill these biological aerosols.

The third conventional method is to coat with a photocatalysis layer to cooperate with a UV light source to activate the photo-catalytic reaction to kill the bacteria. The photocatalysis layer can decompose some biological aerosols (or bacteria) into $CO_2$ and water. Titanium dioxide ($TiO_2$) is a commonly used photocatalysis. While being exposed to UV light or the solar light, it generates free radicals (hydroxyl radicals: OH) and creates electron-hole pairs, so that it can oxidize an organic object. The energy level is 3.2 eV for the anatase form of the titanium dioxide in a photochemical reaction. When titanium dioxide is exposed by the light having the wavelength less than 385 nm, electron will be exerted to the conduction band and leave one electron-hole that reacts with neighboring $H_2O$ and $OH^-$. Therefore, in order to achieve the sterilization effect, the photocatalysis layer must contact with the target (such as the biological aerosols). In this sterilization system, the biological aerosols must contact with those hydroxyl radicals to achieve the function of sterilization.

However, if the filter material is coated with a photocatalysis layer, it does not consider that such system might work due to the bounce effect. Especially, the bounce effect is obvious for those aerosols with larger size. Under this condition, the overall collection efficiency will decrease. If someone wants to coat with a coating layer (to reduce the effect of aerosol bounce off) on the photocatalysis layer, the photocatalytic reaction will not work well due to low contacting portion between biological aerosols and photocatalysis layer. Besides, the photocatalysis layer is quite expensive. If this system is installed in a pipeline of an air conditioning system, it will create many problems. Furthermore, usually UV-A (Ultraviolet A, long wave, or called UVA; 400 nm-315 nm) is applied to activate the photocatalytic reaction. However, the UV-A has a less efficiency to kill the biological aerosols directly. The major function of UV-A is to activate the photocatalytic reaction.

The problems of these conventional methods can be listed below.

[1] It is hard to capture the bioaerosols (a brief term for biological aerosols) with larger size due to the bounce effect. For those bioaerosols with large size, they have high moving velocity due to inertial force. Once they impact on a surface, they tend to bounce off. So, the overall collection efficiency is low. According a study (Aino, N, 1993), the average diameter of virus is about 0.02~0.3 µm. The average diameter of fungal spore or bacteria is about 3~100 µm. For example, small aerosols (such as virus) can be captured by diffusion or electrostatic attraction. Large aerosols (such as fungal spore, bacteria, dust, etc.) can be captured by inertial impaction, interception, and gravitational settling. About the inertial impaction, the objects might be bounce off, so that they still can penetrate through the filter. Particularly, the fungal spore and bacteria can bounce off and spread away via the central air conditioning system in a hospital. It is hard to image how terrible the consequence is.

[2] HEPA is expensive and has high flow resistance. When a HEPA filter is used, the collection efficiency can increase to 99.97% or higher. It seems to be an ideal solution to capture bioaerosols (including the bacteria, fungal spore, pathogens, etc.). It also can avoid the bounce effect. However, the maintenance cost of HEPA filter is too high. Filter in any air conditioning system needs to be replaced periodically. The price of the HEPA filter is approximately ten times higher than the one of a general filter. Besides, because the collection efficiency is high, the collected particles or aerosols will stay in the filter to block the air and then form a blocking portion (or called a dust cake). As a result, the flow resistance is increased without any limit. In order to avoid that, usually the replacement period will be shortened. For example, the maintenance period should be shortened from once a month to twice a month. That means the cost is double per month. In addition, when the flow resistance increases to a certain level, the fan of this air conditioning system will consume more electricity. For example, if someone uses the HEPA filter to replace the general filter, the maintenance at least increases 20 times (10×2). The cost is extremely high.

[3] The sterilization effect is poor. In a traditional air condition system, there is no any sterilization equipment. Although sterilization equipment is installed, it might be installed on at the entrance or the exit of the system. There is no sterilization equipment installed in the middle of the pipeline. For those bioaerosols captured by the filter, they will not die immediately. These bioaerosols are just be stuck at a place. In case of the environment is good for growing up (for example: having enough water (high relative humidity) and nutrition), these stuck bioaerosols still can remain survive, multiply and even reproduce. Hence, that filter becomes the home of bioaerosols. The reproduced bioaerosols also can be widely spread out to more rooms and corners via the pipeline of the air conditioning system. More people might be infected. If the filter is coated with a photocatalysis layer, it does not consider overcoming the bounce effect. Therefore, the collection efficiency for large aerosols is low. The photocatalysis layer is useless, if the filter is covered by another material to reduce the bounce effect, the photocatalysis layer becomes invalid. Besides, the UV-A is used to activate the photocatalyic reaction. The sterilization effect of UV-A is relative lower than UV-C. In addition, the photocatalysis layer must contact with the bioaerosols. If the non-biological aerosols are stuck on some portion of the photocatalysis layer, only the rest portion of the photocatalysis layer still can conduct the photocatalytic reaction. Thus, the overall sterilization effect becomes low. Generally, the non-biological aerosols are more than the biological aerosols in the air. So, the function of photocatalysis layer will be reduced by the non-biological aerosols.

In addition, in the pipeline, all the aerosols are carried by the airstream under the flow velocity about 50~300 cm/s. If one system only utilizes the UV light as the germicidal irradiation, the flow retention time seems too short to let the UV light work well. Furthermore, the pipeline includes many branches and sub-branches. Usually there is no any filtration device or sterilization equipment to capture these aerosols. Besides, aerosols are possible to enter the pipeline, branches or other sub-branches via some connecting gaps, broken holes, cracks, water leaking, and so on. The aerosols can spread out through the pipeline. For example, there are patients, doctors, and nurses in the hospital all the time. It is impossible to vacate the entire hospital to conduct a full-hospital sterilization. Thus, the aerosols stayed in the pipeline might spread out and make all the members (including critical patients, patients in respiratory therapy, hospital workers, etc.) in the hospital to be infected. It is a very serious problem.

SUMMARY OF THE INVENTION

The primary object of the present invention is to provide an air sterilization device with low aerosol bounce. In which, the bounce effect of aerosols can be significantly reduced. Also, the device can sustain the long-term loading effect of high concentration of bioaerosols.

The next object of the present invention is to provide an air sterilization device with low aerosol bounce. The maintenance cost is low.

The other object of the present invention is to provide an air sterilization device with low aerosol bounce. In which, the collection efficiency and sterilization effectiveness of bio-aerosols is good.

Another object of the present invention is to provide an air sterilization device with low aerosol bounce. In which, the flow rate of air conditioning system remains high.

In order to achieve these objects and solve the problems mentioned above, a technical solution is provided. It is an air sterilization device with low aerosol bounce comprising:

an air conditioning pipe having a fixing portion;

a porous filter media secured on the fixing portion, the porous filter media having an entering surface and a leaving surface, the porous filter media having a plurality of irregularly distributed channels, the channels connecting with the entering surface and the leaving surface, the channels being coated with a coating layer having a thickness between 10 µm to 1000 µm for sticking aerosols flow through the channels so as to yield bounce effect; and a UV light generator having at least one UV light generation element and a controller; at least one UV light generation element being disposed near the porous filter media, the controller being able to control the UV light generation element to emit UV light during a predetermined time.

BRIEF DESCRIPTION OF THE DRAWINGS

Figures 3, 4:
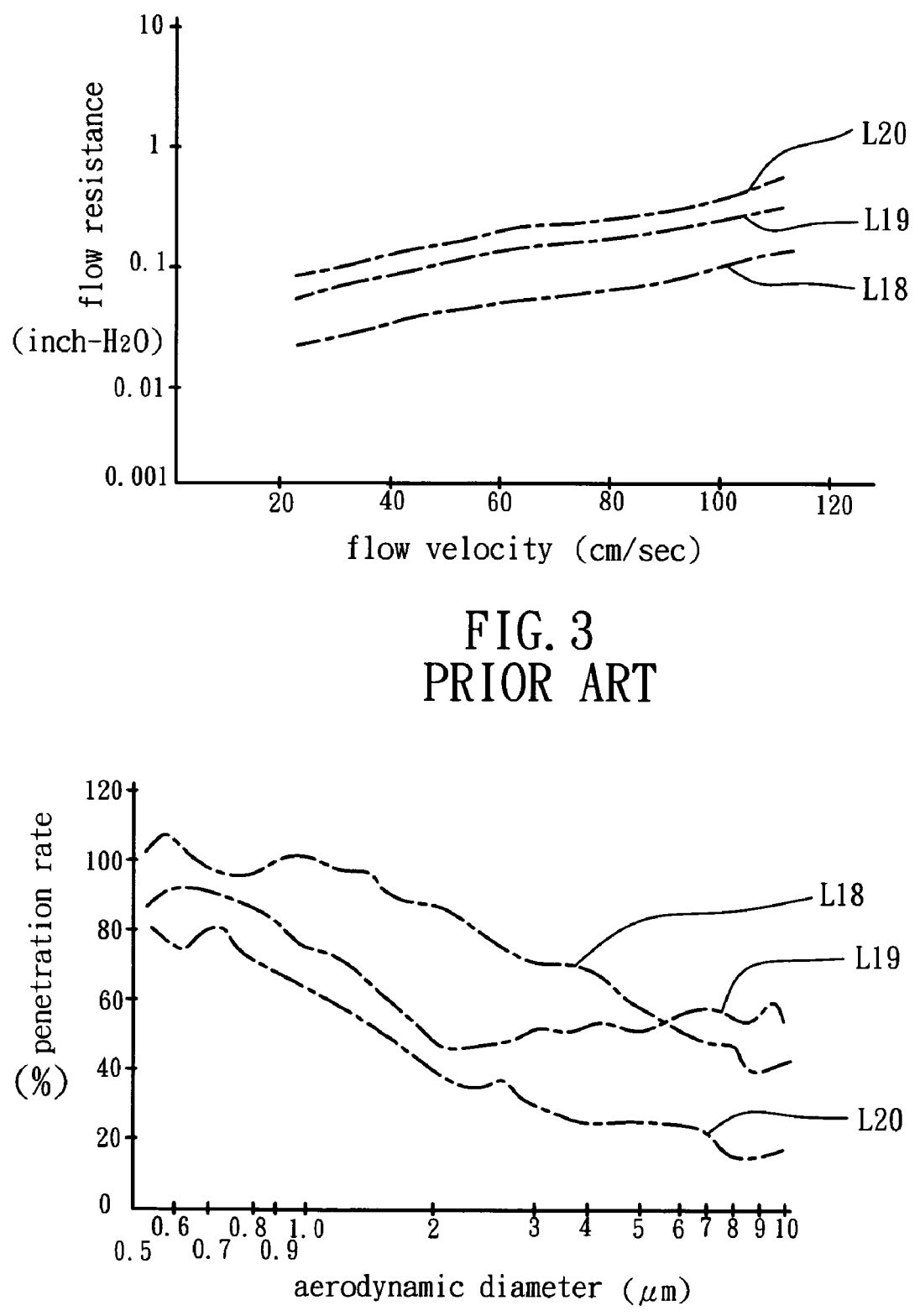

FIG. 3 shows the relationships of flow velocity and flow resistance for a conventional filter.

FIG. 4 shows the relationships of aerodynamic diameter and aerosol penetration rate for a conventional filter.

DETAILED DESCRIPTION OF THE PREFERRED EMBODIMENT

Figure 1:
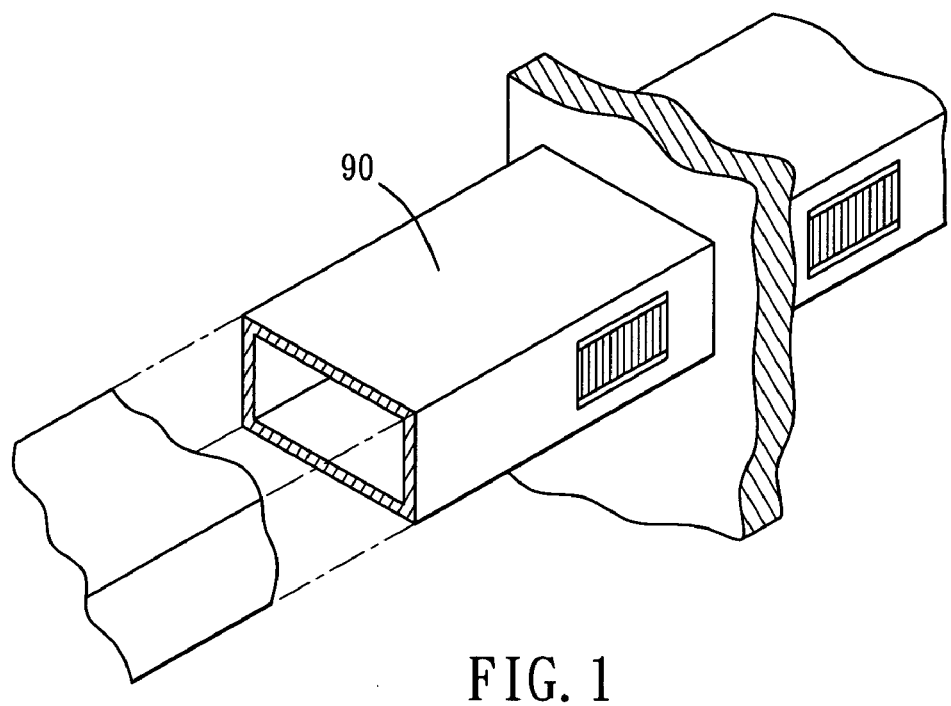
FIG. 1 is a view showing a pipeline of a conventional air conditioning system.
Figure 2:
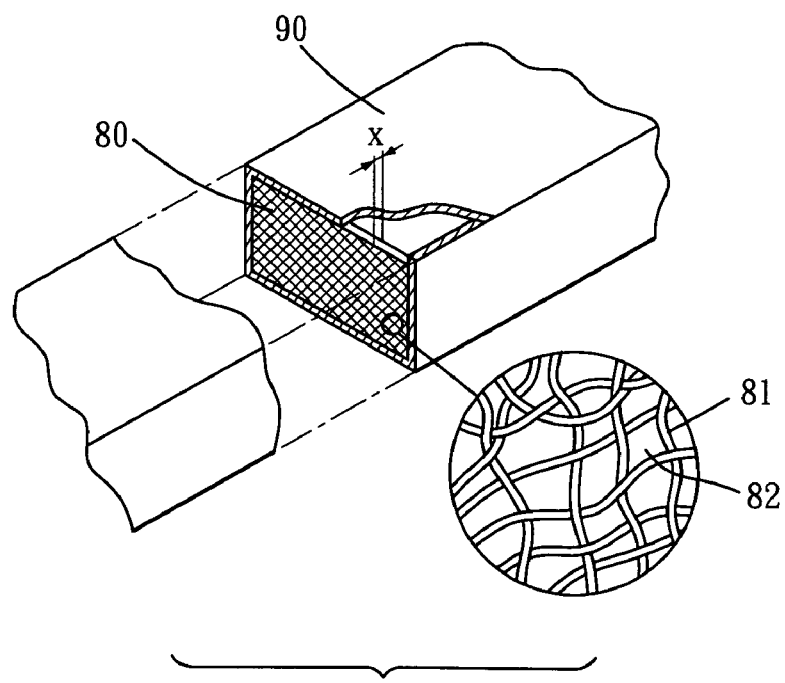
FIG. 2 is another view showing a pipeline with a filter of a conventional air conditioning system.
Figure 5:
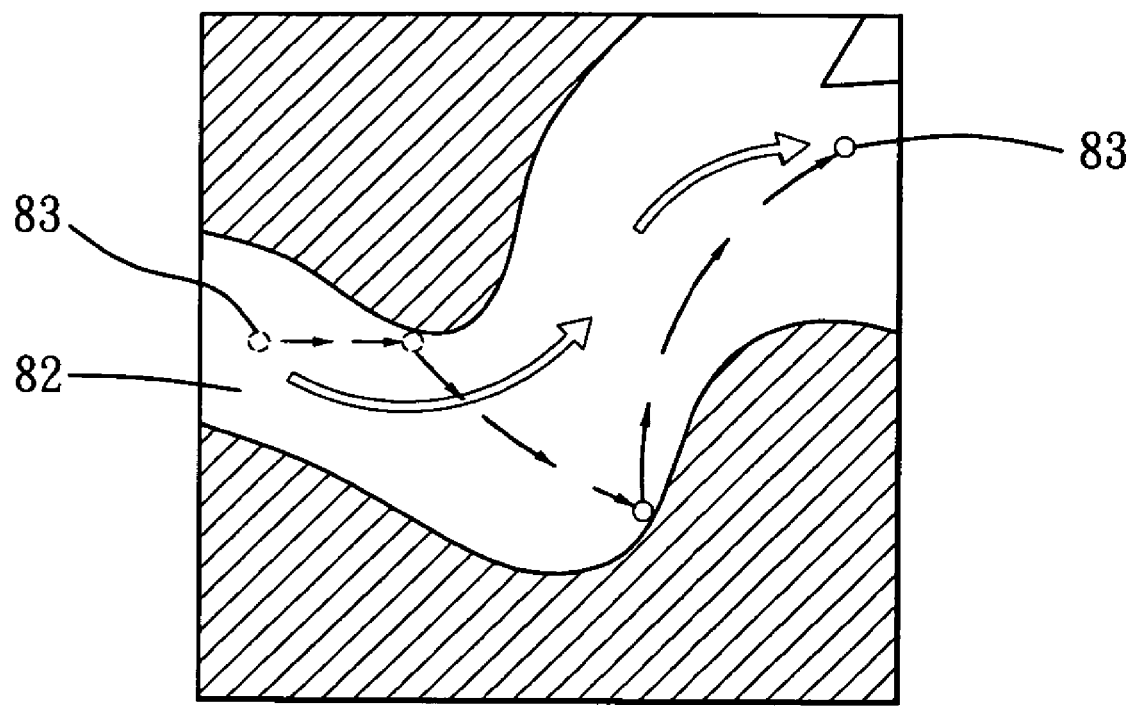
FIG. 5 is a schematic view showing the bounce effect in a conventional system.
Figure 6:
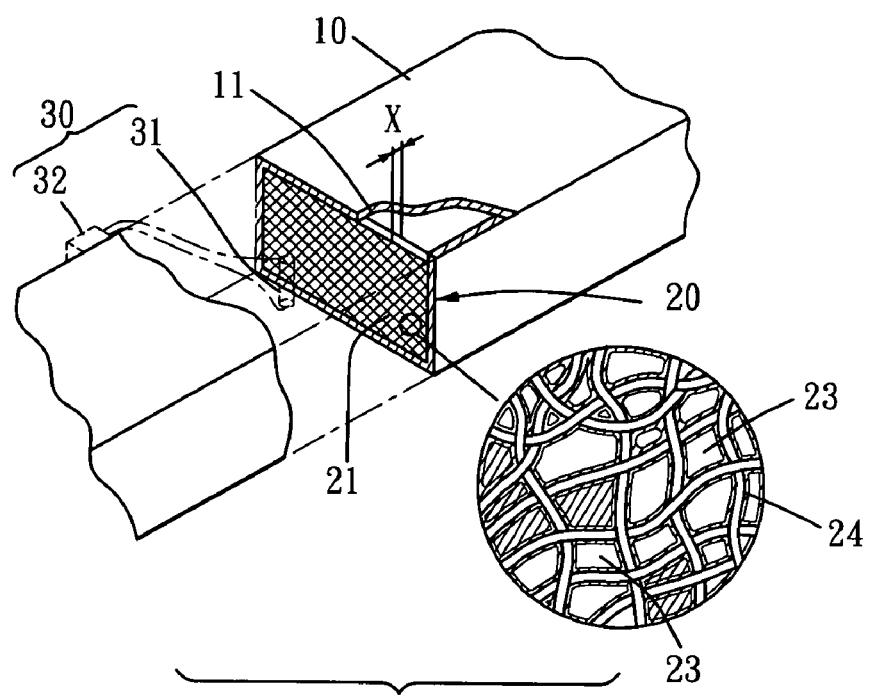
FIG. 6 is a view showing a preferred embodiment of the present invention.
Figure 7:
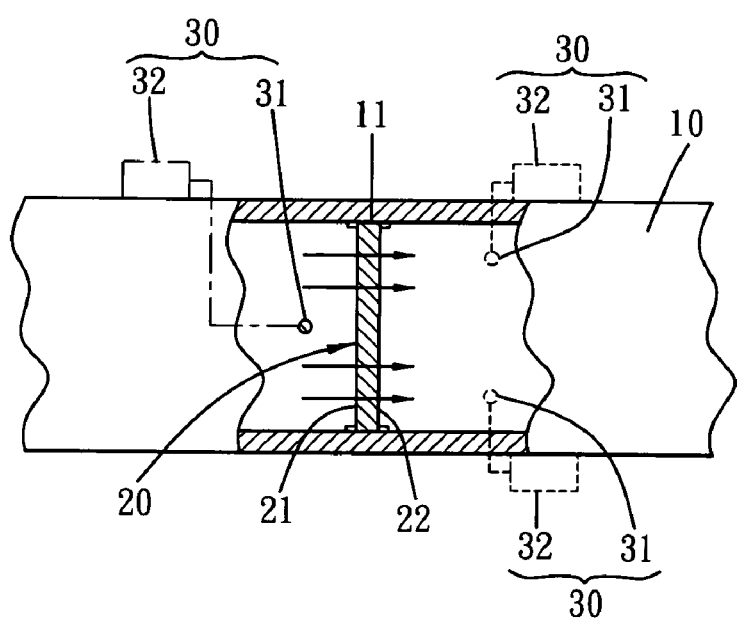
FIG. 7 is a view of a selected portion of the present invention.

Referring to FIGS. 6 and 7, the present invention is an air sterilization device with low aerosol bounce. It mainly comprises an air conditioning pipe 10, a porous filter media 20, and a UV light generator 30.

With regard to this air conditioning pipe 10, it has a fixing portion 11.

Figure 8:
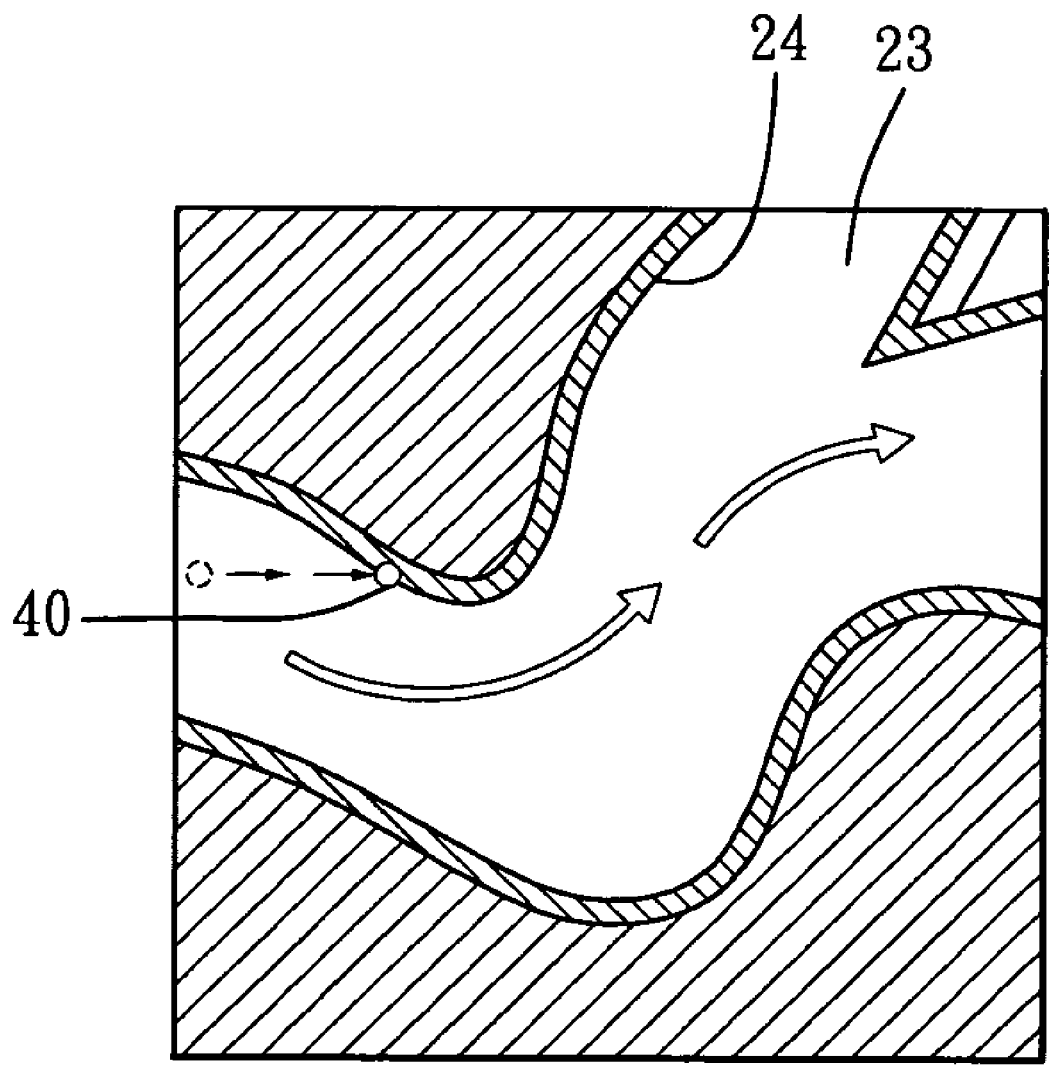
FIG. 8 is a schematic view showing the no bounce effect in this invention.

About this porous filter media 20, it is secured on the fixing portion 11. This porous filter media 20 has an entering surface 21 and a leaving surface 22. The porous filter media 20 has a plurality of irregularly distributed channels 23. The channels 23 connect with the entering surface 21 and the leaving surface 22. In this embodiment, the porous filter media 20 is made by a porous material (such as foam) about 80 ppi (pores per inch). The channels 23 is coated with a coating layer 24 (such as an oil film, grease layer or the like with low viscosity) having a thickness between 10 μm to 1000 μm for absorbing aerosols 40 (with large inertial force) flow through the channels 23 (in the air conditioning pipe 10) so as to yield bounce effect (as illustrated in FIG. 8).

Concerning the UV light generator 30, it has at least one UV light generation element 31 and a controller 32. At least one UV light generation element 31 is disposed near the porous filter media 20. The controller 32 is able to control the UV light generation element 31 to emit UV light during a predetermined time. For example, UV light generation element 31 can emit UV light having the wavelength of 254 nm and with the energy of 18 watt. Of course, more than one UV light generation element 31 is possible. The installed position can be adjusted (such as upstream, downstream, or both). It is flexible to alter the number or the position. As exhibited in FIG. 7, the UV light generation element 31 is installed in an upstream zone (ahead of the porous filtration position 20). Of course, the user can install two UV light generation elements 31 in a downs stream zone (behind the porous filter media 20).

The Table 1 listed below is the result of an experiment of *Escherichia coli* (can be briefly referred as *E. coli*). A simplify unit: single layer foam (thickness: 12 mm) combine with single UV light generator is used in the experiment. The face velocity of the unit is 100 cm/s. Before the UV light generation element 31 is activated, the collection results for *E. coli* in the upstream of the unit is 103.5 cfu/m$^3$ (colony forming unit, cfu). The collection results for *E. coli* in the downstream of the unit is 26.9 cfu/m$^3$. But, after the UV light generation element 31 is activated, the collection results for *E. Coli* in the upstream of the unit is 26.6 (it means the sterilization rate is 74.3%). The collection results for *E. coli* in the downstream is 0.3 (it means the total sterilization rate is 98.9%). Thus, the sterilization effect of this invention is excellent.

TABLE 1

| Item | Upstream zone (CFU/m$^3$) | Downstream zone (CFU/m$^3$) |
|---|---|---|
| Before activating the UV light generation element | 103.5 | 26.9 |
| After activating the UV light generation element | 26.6 | 0.3 |
| sterilization rate | 74.3 (%) | 98.9 (%) |

As shown in FIGS. 6, 7 and 8, the porous filter media 20 is secured on the fixing portion 11 of the air conditioning pipe 10. Air flows through the porous filter media 20. First, the air enters from the entering surface 21 (as illustrated in FIG. 6) and then exits from the leaving surface 22. Many aerosols 40 (such as fungal spore, bacteria, pathogens, etc.) are carried by the airstream. Airstream tends to easily change floe direction when moves through a curvy path in one of the channels 23, however, some large aerosols 40 impact the inner surface of the channels 23 due to inertial force. Because there is a coating layer 24, the impacted aerosols 40 will be stuck by the coating layer 24. That is, the aerosols 40 will not bounce away. Hence, the coating layer 24 significantly reduces the aerosol bounce effect. If there are enough irregularly distributed channels 23, it is highly possible that most aerosols 40 will be adhered or stuck by the coating layer 24 so as to substantially eliminate the bounce effect.

Also, by activating this UV light generator 30 for a period of time, the UV light generation element 31 emits high intensity UV light to kill the aerosols 40 (including fungal spore, bacteria, etc.). It is optional to increase the quantity, the activating time and wattage of the UV light generation element 31. Under this condition, because these aerosols 40 are stayed on the coating layer 24, more aerosols 40 will be killed by this constant emitting UV light. If the aerosols 40 quickly pass through the UV light zone without any filtration, the sterilization effect will not be significant, especially in a high flow velocity air condition system.

In addition, the porous filter media 20 can be foam with low thickness. By utilizing the combination of foam and UV light generation element, it still has a great performance with good filtration efficiency and excellent sterilization rate. With regard to the relationships among the porous filter media thickness, channel (pore) size, flow velocity and aerosol penetration rate, they can be tested by the following experiments.

Figure 9:
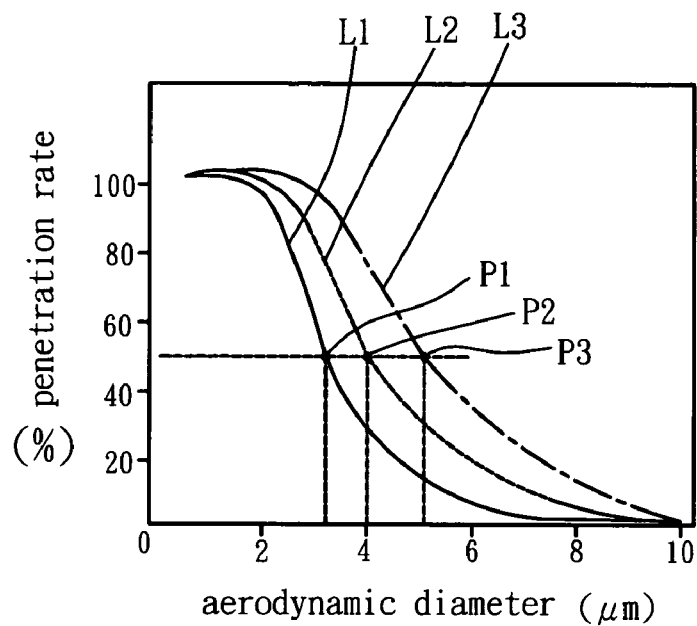
FIG. 9 shows the relationships about porous filter media thickness, pore size, aerodynamic diameters, and penetration rate of this invention.

As illustrated in FIG. 9, the operation parameters are: the pore size (briefly called N) of the porous filter media 20 (see FIGS. 6 and 7) is set at N=110 ppi and the flow velocity (briefly called U) is fixed at U=27.2 cm/s. The first curve L1, second curve L2 and third curve L3 represent the porous filter media thickness (briefly called X) of 20 mm, 10 mm and 5 mm respectively. If the penetration rate is fixed at 50% as a reference line, this reference line intersects with the first curve L1, second curve L2 and third curve L3 at three points, namely the first point P1, second point P2 and the third point P3. These points mean the corresponding aerodynamic diameters ($d_{ae}$) are 3 μm, 4 μm, and 5 μm. Therefore, if the thickness of the porous filter media 20 is thicker, the filtration effect is better. When the thickness is increased from 5 mm to 20 mm, the penetration rate of aerodynamic diameters ($d_{ae}$) of 3 μm is decrease from 95% to 50%. Based on this result, if the thickness is increased more, the corresponding penetration rate will be lower than 50%.

Figure 10:
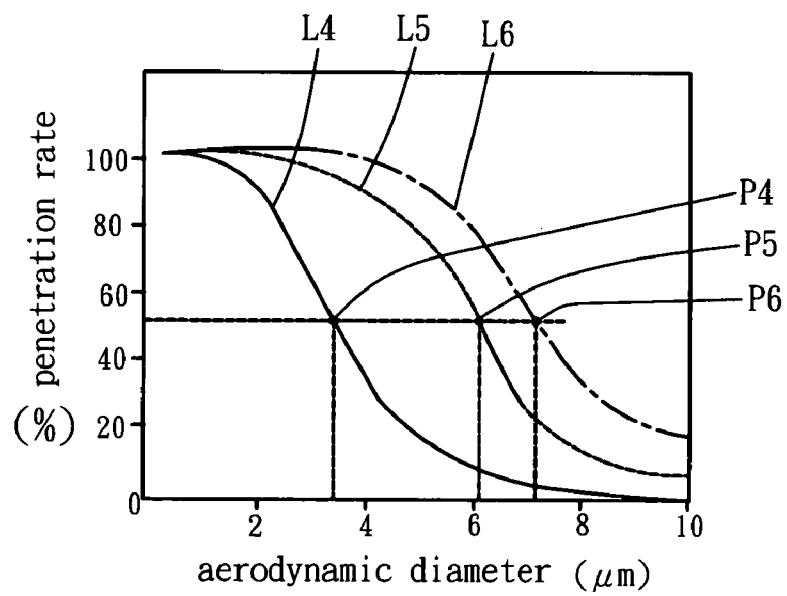
FIG. 10 shows the relationships about porous filter media thickness, flow velocity, aerodynamic diameters, and penetration rate of this invention.

Referring to FIG. 10, the controlled conditions are: the thickness of the porous filter media 20 (see FIGS. 6 and 7) is fixed at x=10 mm and the flow velocity is set at U=27.2 cm/s. The fourth curve L4, fifth curve L5 and sixth curve L6 represent the pore size (N value) of the porous filter media at N=110 ppi, 80 ppi and 45 ppi respectively. If the penetration rate is fixed at 50% as a reference line, this reference line intersects with the fourth curve L4, fifth curve L5 and sixth curve L6 at three points, namely the fourth point P4, fifth point P5 and the six point P6. These points mean the corresponding aerodynamic diameters ($d_{ae}$) are 3.5 μm, 6.3 μm, and 7.5 μm. Therefore, if N value (pores per inch) of the porous filter media 20 is larger (means the hole is smaller), the filtration effect is better. When the N value of the porous filter media 20 is increased, the penetration rate of aerodynamic diameters ($d_{ae}$) of 3 μm is decreased accordingly. Theoretically, if the thickness is increased more, the corresponding penetration rate will be lower. Thus, the aerosol collecting efficiency becomes better.

Figure 11:
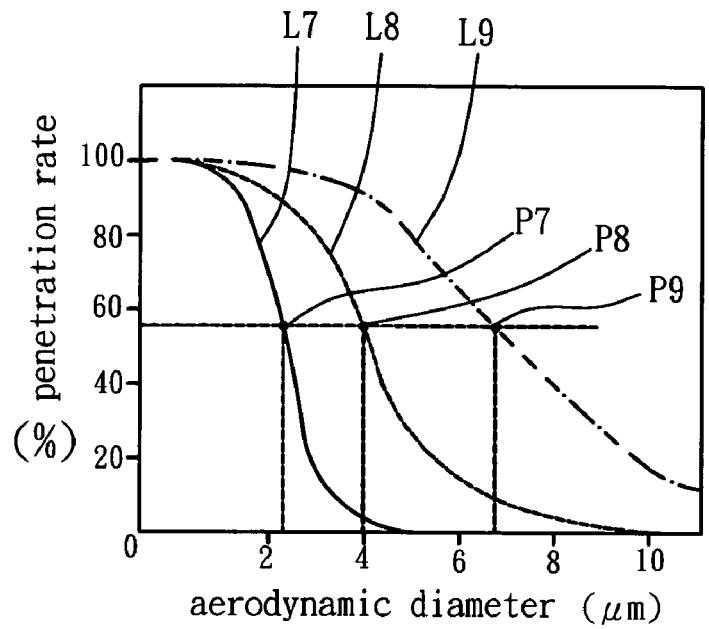
FIG. 11 shows the relationships about porous filter media thickness, pore size, flow velocity, aerodynamic diameters, and penetration rate of this invention.

As shown in FIG. 11, the controlled conditions are: the thickness of the porous filter media 20 (see FIGS. 6 and 7) is held at x=10 mm and the pore size (N value) of the porous filter media 20 is fixed at N=110 ppi. The seventh curve L7, eighth curve L8 and ninth curve L9 represent the data when the flow velocity is tested at U=54.3 cm/s, 40.7 cm/s and 27.2 cm/s respectively. If the penetration rate is fixed at 50% as a reference line, this reference line intersects with the seventh curve L7, eighth curve L8 and ninth curve L9 at three points, namely the seven point P7, eight point P8 and the ninth point P9. These points that represent the corresponding aerodynamic diameters ($d_{ae}$) are 2.5 μm, 4.1 μm, and 6.5 μm. Therefore, if the flow velocity increases, the inertial force is increased. Hence, more aerosols with high inertial force tend to impact on the coating layer. As a result, the filtration rate (collection efficiency) becomes significant. When the filter thickness is increased from 5 mm to 20 mm, the penetration rate of aerodynamic diameters ($d_{ae}$) of 3 μm is decrease from 95% to 50%. Based on this result, when the flow velocity increases, the filter filtration rate also increases.

Figure 12:
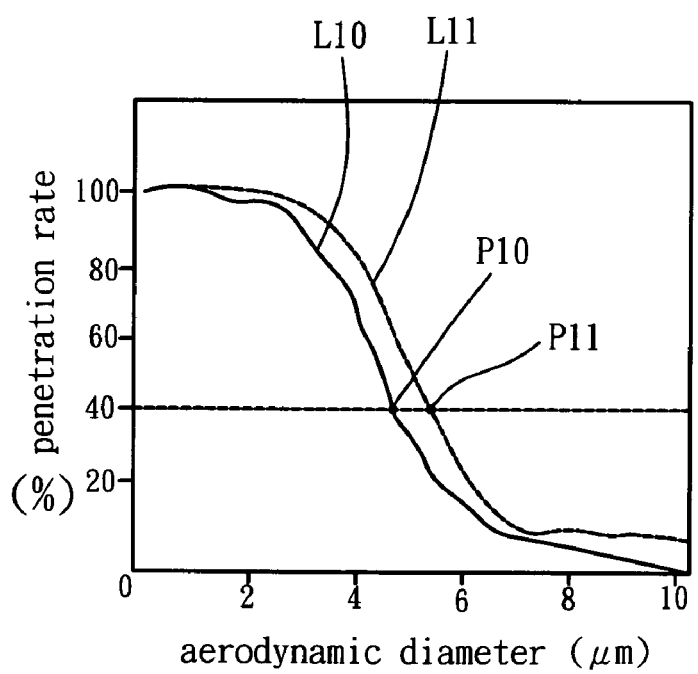
FIG. 12 illustrates the relationships about porous filter media thickness, pore size, aerodynamic diameters, and penetration rate of this invention.

As exhibited in FIG. 12, the operation parameters are: the thickness of the porous filter media 20 (see FIGS. 6 and 7) is controlled at x=10 mm and the pore size (N value) of the porous filter media 20 is fixed at N=40 ppi. The tenth curve L10 and eleventh curve L11 represent the porous filter media 20 with the coating layer 24 and without the coating layer 24 respectively. If the penetration rate is fixed at 40% as a reference line, this reference line intersects with the tenth curve L10 and eleventh curve L12 at two points, namely the tenth point P10 and eleventh point P11. These points mean the corresponding aerodynamic diameters ($d_{ae}$) are 4.5 μm and 5.3 μm. The results prove that the porous filter media 20 with the coating layer 24 has high collection efficiency than without the coating layer 24. Particularly, if only observes a range of the aerodynamic diameters between 6~10 μm, the eleventh curve L11 (without the coating layer 24) still fluctuating around 5% to 10%, because there is no any coating layer 24 to avoid the bounce effect for large aerosols. Therefore, it can be proved that the coating layer 24 can substantially avoid the bounce effect so as to minimize the penetration rate down to almost 0%.

Figure 13:
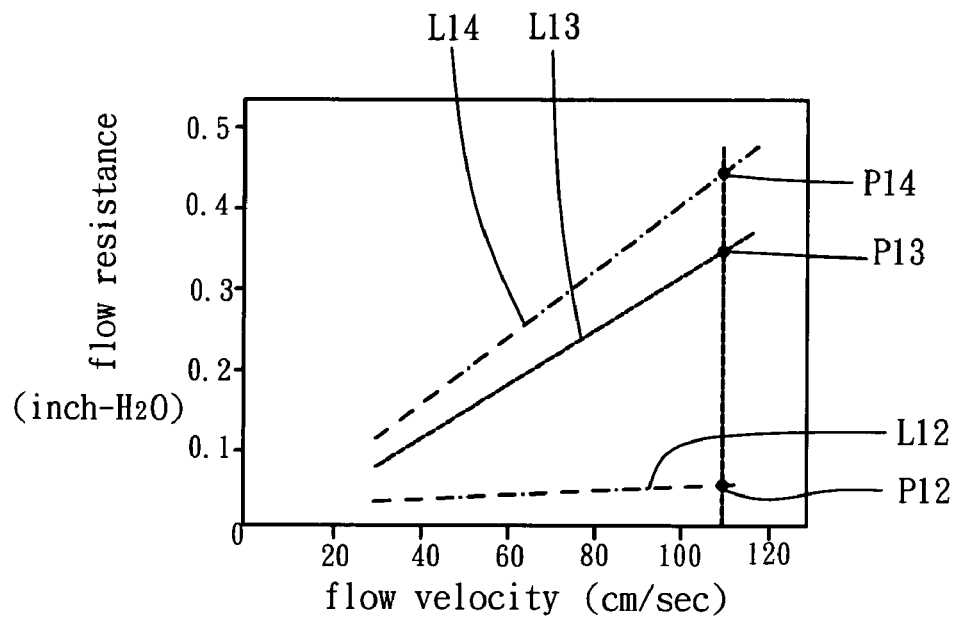
FIG. 13 shows the relationships about pore size, flow velocity, aerodynamic diameters, and flow resistance of this invention.

FIG. 13 shows that the twelfth curve L12, thirteenth curve L13 and fourteenth curve L14 represent the pore size (N values) of porous filter media 20 are held at 110 ppi, 80 ppi and 45 ppi respectively. According these curves, the flow resistance is proportional to flow velocity. When air flows through the porous filter media 20, the flow is laminar (not turbulent). In addition, the flow resistances from the smallest one to the largest one can be seen as the twelfth point P12, thirteenth point P13 and the fourteenth point P14.

Figure 14:
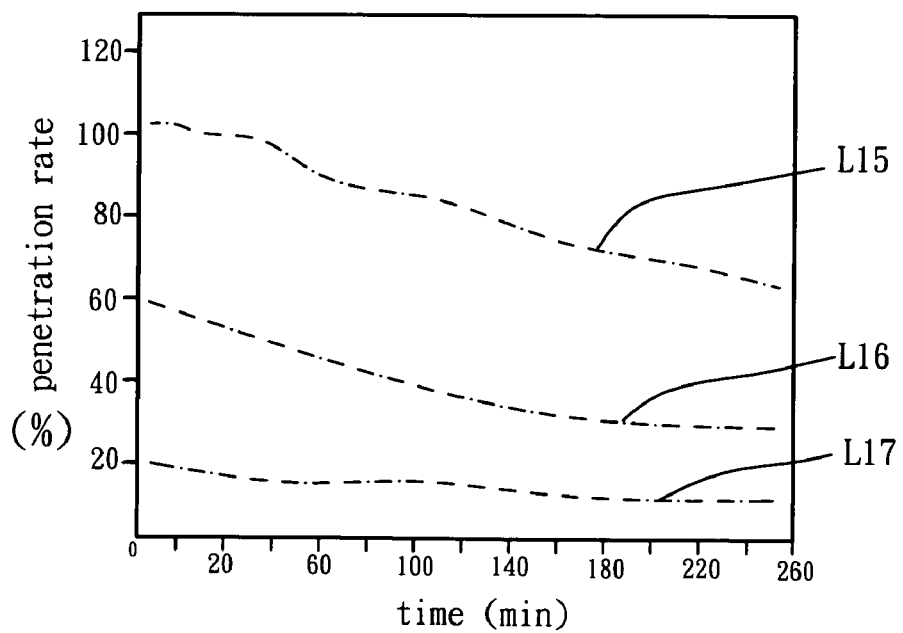
FIG. 14 shows the relationships about aerodynamic diameters, time and penetration rate of this invention.

FIG. 14 illustrated the experimental diagram about the penetration rate for aerosols. In which, the fifteenth curve L15, sixteenth curve 16, and the seventeenth curve L17 represent the results of the aerosols having the aerodynamic diameters of 1.75 μm, 2.888 μm and 2.642 μm. All the penetration rates gradually decrease as time increases. That is, this invention is suitable for most biological aerosols and it can be used for long-term collection.

By increasing the N value, the flow velocity of the porous filter media 20, the filtration rate increases.

Moreover, since this invention can capture these aerosols 40 (including fungal spore, bacteria, etc.) and kill these aerosols 40 by UV light, there is no need to utilize any expensive photocatalysis for increasing the sterilization effect. Thus, the entire cost for this invention can be lowered down significantly.

The advantages and functions of this invention can be summarized as follows.

[1] The bounce effect of aerosols can be significantly reduced. In this invention, there are a lot of irregular channels having coating layer. When the aerosols (including fungal spore, bacteria, etc.) are carried by the airstream, most aerosols will be filtered by single fiber theory as described before. Large aerosols with significant inertial force will impact on the coating layer of the filter media. Once the aerosols impact on the coating layer, they will be stuck (or fixed) on. Therefore, the bounce effect of aerosols can be considerably reduced.

[2] The maintenance cost is low. The porous filter media 20 contains a lot of irregular-distributed channels (such as formed in porous foam or the like). The thickness (the filter volume) of the porous filter media 20 can be properly increased, if needed. Also, it can be modified as multiple ones with UV light generators in order to increase the filtration rate and the sterilization effect. Plus, the coating layer can avoid the bounce effect of large aerosols, and it is unnecessary to utilize the expensive photocatalysis. Therefore, the manufacture for this invention is easy, and the entire cost is low, too. Besides, if the porous filter media 20 is made of metal, it can be washed and reused. Thus, the overall product service life is prolonged. Under the same maintenance standard, the overall maintenance cost for this invention is relative low than other sterilization methods.

[3] The sterilization effect is excellent. This invention can capture the aerosols and kill them by UV light. In addition, it can prevent the captured aerosols to keep alive (even to survive and to reproduce). Thus, the sterilization effect of this invention is excellent.

[4] The flow rate of the air conditioning system remains high. If increasing the cross sectional filtration area of the porous filter media, the overall flow rate will be raised. Also, the flow resistance can be reduced. It is good for an air conditioning system. Moreover, once the flow velocity is increases, the inertial force of the aerosol increases. Hence, it can capture more aerosols. The collection efficiency can be increased.

What is claimed is:

1. An air sterilization device with low aerosol bounce comprising:
    an air conditioning pipe having a fixing portion;
    a porous filter media secured on said fixing portion, said porous filter media having an entering surface and a leaving surface, said porous filter media having a plurality of irregularly distributed channels, said channels connecting with said entering surface and said leaving surface, said channels being coated with a coating layer having a thickness between 10 μm to 1000 μm for trapping aerosols flowing through said channels so as to minimize said aerosols from bouncing off said channels; and
    a UV light generator having at least one UV light generation element and a controller; at least one UV light generation element being disposed near said porous filter media, said controller selectively enabling said UV light generation element to emit a specific wavelength and energy at a predetermined time.

2. The air sterilization device with low aerosol bounce as claimed in claim 1, wherein said porous filter media is a porous material.

3. The air sterilization device with low aerosol bounce as claimed in claim 1, wherein said coating layer is selected from an oil film or a grease layer with low viscosity.

4. The air sterilization device with low aerosol bounce as claimed in claim 1, wherein at least one UV light generator is disposed in an upstream zone of said porous filter media, at least one UV light generator is disposed in an downstream zone of said porous filter media; and one or more said porous filter media and said UV light generators are disposed in series.

5. The air sterilization device with low aerosol bounce as claimed in claim 1, wherein at least one UV light generator is disposed in an upstream zone of said porous filter media, at least one UV light generator is disposed in an downstream zone of said porous filter media; and one or more said porous filter media and said UV light generators are disposed in parallel.

6. The air sterilization device with low aerosol bounce as claimed in claim 1, wherein each of said channels define a pore size between 80 and 110 pores per inch (ppi) and a thickness between 10 and 20 mm, and a flow velocity in said air conditioning pipe is at least 54.3 cm/s.

* * * * *